United States Patent [19]

Manser et al.

[11] Patent Number: 5,214,166

[45] Date of Patent: May 25, 1993

[54] METHOD OF SYNTHESIZING NITRATO ALKYL OXETANES

[75] Inventors: Gerald E. Manser, El Dorado Hills, Calif.; Robert M. Hajik, Willard, Utah

[73] Assignee: The United States of America as represented by the Secretary of the Navy, Washington, D.C.

[21] Appl. No.: 377,398

[22] Filed: Jul. 10, 1989

Related U.S. Application Data

[63] Continuation-in-part of Ser. No. 925,655, Nov. 29, 1986, abandoned.

[51] Int. Cl.$^5$ ............................................. C07D 305/04
[52] U.S. Cl. ................................................... 549/510
[58] Field of Search ................................ 549/510, 464

[56] References Cited

U.S. PATENT DOCUMENTS

| | | | |
|---|---|---|---|
| 3,932,412 | 1/1976 | Simpson | 546/90 |
| 4,431,830 | 2/1984 | Schönafinger | 549/464 |
| 4,683,086 | 7/1987 | Frankel et al. | 549/510 |

Primary Examiner—C. Warren Ivy
Assistant Examiner—Ba K. Trinh
Attorney, Agent, or Firm—Thomas E. McDonnell; Barry A. Edelberg; A. David Spevack

[57] ABSTRACT

Nitrato alkyl oxetanes are synthesized directly from the corresponding hydroxy alkyl oxetanes by nitrating the hydroxy alkyl oxetane under non-acidic anhydrous conditions. A hydroxy alkyl oxetane is reacted with an anhydrous nitrate ester of a carboxylic acid at temperatures below about 10° C. The product of the method, nitrato alkyl oxetane, is produced in relatively high yield without opening of the oxetane ring.

14 Claims, No Drawings

METHOD OF SYNTHESIZING NITRATO ALKYL OXETANES

This application is a continuation-in-part of application Ser. No. 06/925,655, filed Nov. 29, 1986, now abandoned.

BACKGROUND OF THE INVENTION

1. FIELD OF THE INVENTION:

This invention relates to a method of synthesizing nitrato alkyl oxetanes.

2. DESCRIPTION OF THE PRIOR ART:

Energetic polymers are of particular interest in providing energetic elastomers which are suitable for use in binder systems of high-energy compositions, such as propellants, explosives, and gasifiers. For example, high-energy polyethers are curable with isocyanates to form elastomers suitable for use as propellant binders. High energy polyethers and elastomers formed by curing the same have the further advantage of being miscible with high-energy nitroester plasticizers, such as nitroglycerine, butanetriol trinitrate and trimethylolethane trinitrate. A nitroester-plasticized polyether elastomer containing high-energy mer units can provide a binder system which is inherently very high in energy.

U.S. Pat. No. 4,483,978 ('978), issued to Manser on Nov. 20, 1984, the teachings of which are incorporated herein by reference, describes in detail azido alkyl oxetanes and polyethers and cured elastomers derived therefrom. '978 also discloses that other energetic substituents in oxetanes include nitro and nitrato groups. While azido derivatized oxetanes, such as azido methyl methyl oxetane (AMMO) and bis (azidomethyl) oxetane (BAMO), are of interest, they cannot provide the level of propellant performance that nitrato- and nitro-derivatized oxetanes, such as nitrato methyl methyl oxetane (NMMO) and bis (nitratomethyl) oxetane (BNMO), can provide. For instance, the specific impulse of a BAMO/AMMO system with an oxygen to fuel ratio of 1.053 to 1 is about 1.4 while the specific impulse of a BNMO/BAMO system with an oxygen to fuel ratio of 1.122 to 1 is about 1.8. Smoke propellant results can be even more dramatic in some cases, showing an impulse increase of up to six seconds when nitrato- and nitro-derivatized oxetanes are used instead of azido-derivatized oxetanes.

However, nitrato-derivatized oxetanes have not been used to any significant extent in binders for high-energy compositions because there does not exist a practical synthesis for such compounds. The accepted literature method of producing nitrato alkyl oxetanes, specifically 3,3-Bis (nitratomethyl) oxetane, by nitrating a reaction mixture of trisnitrato pentaerythritol via an equal mixture of 80% nitric acid and 80 % sulfuric acid. This is unacceptable for large scale production of nitrato-derivatized oxetanes because the method results in the opening of the oxetane ring. The ring must be subsequently closed with sodium ethoxide in order to obtain the product. Additionally, although the method is reproducible, it produces uncontrolled fume-off during the nitration step and near explosive conditions.

Direct nitration of the hydroxyl alkyl oxetanes would avoid this circuitous route, but as the oxetane ring structure is highly strained, ring opened products are thermodynamically favored and tend to result, particularly under the highly acidic conditions under which most nitrations are conducted.

SUMMARY OF THE INVENTION

Accordingly, it is an object of this invention to provide a method of synthesizing nitrato alkyl oxetanes that is suitable for large scale production of such compounds.

It is also an object of this invention to provide a method of synthesizing nitrato alkyl oxetanes that is reproducible with relatively high yields.

It is also an object of this invention to provide a method of synthesizing nitrato alkyl oxetanes in which the oxetane ring does not open.

It is a further object of this invention to provide a method of synthesizing nitrato alkyl oxetanes that does not result in uncontrollable fume-off and explosive conditions.

These and additional objects of the invention are accomplished by reacting anhydrous nitrate-containing compounds with an anhydrous carboxylic acid derivative to form an anhydrous nitrate ester of the carboxylic acid. The anhydrous nitrate ester is reacted with a hydroxy alkyl oxetane in order to nitrate the hydroxy alkyl oxetane under non-acidic conditions at temperatures of about 10° C. or lower to yield the corresponding nitrato alkyl oxetane.

DETAILED DESCRIPTION OF THE INVENTION

The method of the invention begins with the formation of an anhydrous nitrate ester of a carboxylic acid which will then be reacted with a hydroxyl alkyl oxetane under non-acidic anhydrous conditions in order to nitrate the hydroxyl alkyl oxetane and form a nitrato alkyl oxetane. This anhydrous nitrate ester will act as a non-acidic nitrating agent in the method. The nitrate ester must be anhydrous and is formed from an anhydride of a carboxylic acid and a nitrate-containing compound. The nitrate-containing compound must be one that will produce an anhydrous nitrate ester when reacted with the anhydride of the carboxylic acid. It is preferable to select the nitrate-containing compound from the group consisting of between about 90and 100% nitric acid and nitrogen pentoxide. Most preferred is about 90% nitric acid. Preferably, the carboxylic acid has the general formula R—COOH wherein R is selected from the group comprising alkyl and aryl moieties. It is most preferred to use R—COOH where R is a methyl group (acetic acid). It is imperative that the nitrate ester selected will not cause acid hydrolysis of the hydroxyl alkyl oxetane since the hydroxyl alkyl oxetane is extremely sensitive to hydrolysis and the oxetane ring will open upon hydrolysis. In forming the anhydrous nitrate ester, it is preferable to have an excess of the anhydride so that the resulting anhydrous nitrate ester will be handled in a solution of anhydride. This is preferred for safety reasons since isolation of the pure anhydrous nitrate esters may cause an explosive situation. A molar ratio of about 2:1 (anhydride:nitrate-containing compound) is most preferred.

The nitration of the hydroxyl alkyl oxetane can be carried out in any organic solvent that is not hygroscopic, as any water present in the method will cause hydrolysis, opening the oxetane ring and hindering the reaction. The solvent must also be unreactive with the nitrate ester. It is preferable to use chlorinated hydrocarbons as solvents. It is most preferable to use a solvent selected from the group of methylene chloride, chloroform and mixtures thereof. Preferably, the nitrate ester is present in excess of the hydroxyl alkyl oxetane so that a high yield of the nitrated product is obtained. It is most preferred to have a nitrate ester to hydroxyl alkyl oxetane ratio of about 1.5 to 1 or greater.

The hydroxyl alkyl oxetane to be nitrated has the general formula:

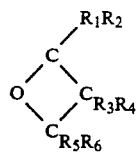

wherein at least one of $R_1$-$R_2$ is —$(CH_2)_n$—CHOH—A, wherein n is one or greater and A is selected from the group comprising H and alkyl groups and the remainder of $R_1$-$R_2$ are selected from the group comprising H and alkyl. Preferably, A is H, so that the oxetane being nitrated is a primary alcohol. It is also preferred that n be from about one to three. Most preferably, the hydroxy alkyl oxetane is 3,3-Bis(hydroxymethyl)oxetane or 3-hydroxymethyl oxetane.

In order to minimize ring opening, it is preferred to dilute the hydroxy alkyl oxetane prior to adding the nitrate ester. A solution of about 20 percent hydroxy alkyl oxetane in solvent (weight/weight) is most preferred. While adding the nitrate ester to the hydroxy alkyl oxetane, the reaction temperature should be kept between about 10° and −20° C. to avoid opening the oxetane ring, increase product yield and ensure a controlled reaction rate. It is preferred to keep the reaction temperature between about 10° and −10° C., with 0° C. being most preferred. The nitrate ester must be added at such a rate that the reaction temperature does not fluctuate more than 5° C.

After the nitrate ester has been added, the product of the method, nitrato alkyl oxetanes, may be removed by any conventional method such as extraction. Preferably, any excess reactants, such as the nitrate ester, are neutralized to quench the reaction prior to extraction.

The products of the method, nitrato alkyl oxetanes, may be polymerized to form polyethers according to the method taught in U.S. Pat. No. 4,393,199 issued to Manser in July 1983. The nitrato alkyl oxetanes can be used to form homopolymers or may be copolymerized with one or more cyclic ethers, including ethylene oxide, other oxetanes and with tetrahydrofuran and tetrahydrofuran derivatives. The polymers so produced are curable, for example, with isocyanates and cross-linking agents to form elastomers.

Having described the invention, the following examples are given to illustrate specific applications of the invention. These specific examples are not intended to limit the scope of the invention described in this application.

EXAMPLE 1

Preparation of 3-nitratomethyl-3-methyloxetane

Into a 12 liter, three-neck flask, fitted with a stirrer, Snyder distilling column, and immersion thermometer, were placed 4712 g (39.22 mole) of 1,1,1-tris(hydroxymethyl)ethane, 4900 ml (41.5 mole) of diethylcarbonate, and 11.7 g of potassium hydroxide dissolved in 47 ml of ethanol. The mixture was heated to 105° C., and the ethanol which formed slowly distilled at a head temperature of 73° to 75° C. When the distillation slowed, the system was connected to a vacuum pump and the pressure was slowly reduced to remove any remaining ethanol and diethylcarbonate. The pot temperature was raised to 160° C. and the pressure further reduced until $CO_2$ evolved. When the evolution of $CO_2$ slowed, the pressure was reduced to 0.3 mm Hg (absolute pressure), the product distilling at a head temperature of 110° C. giving a total weight of 3419 g of 3-hydroxymethyl-3-methyloxetane.

An acetyl nitrate solution was prepared by adding, with stirring, 208 ml of 90-percent nitric acid to 900 ml of acetic anhydride at 20° C. This solution was then cooled to 5° C. and added slowly with vigorous stirring to a solution of 438 g of 3-hydroxymethyl-3-methyloxetane in 1200 ml of chloroform. The temperature was maintained at −10° C. during the addition and for a further 15 to 30 minutes thereafter. The reaction was quenched by pouring over 900 g of sodium bicarbonate followed by the addition of water and very rapid stirring. When the pH of subsequent bicarbonate-water washings remained at 7 to 8, the organic layer was washed with distilled water and dried over magnesium sulfate. The required product was obtained in polymerizable purity by passing it through a basic alumina column, diluting with 50/50 vol/vol chloroform/hexane. The final yield was 416 g. Elemental analysis confirmed that the product was 3-nitratomethyl-3-methyloxetane.

EXAMPLE 2

Preparation of 3,3-Bis (nitratomethyl)oxetane

Into a 2 liter, three-neck flask, fitted with a stirrer, Snyder distillation column, and thermometer, 307 g (1.52 mole) of 3,3-bis(acetoxymethyl)oxetane and 790 ml of methanol were added. The flask was heated to a temperature of 45° C. at which time 1.6 g (0.03 mole) of sodium methoxide was added. The solution was heated to reflux and the methyl acetate produced distilled at a head temperature of 52° C. After the methyl acetate distillation ceased, the solution was cooled to room temperature and neutralized to pH 7 with HCl. The methanol was removed by evaporation and 3,3-bis (hydroxymethyl)oxetane (BHMO) was distilled at a head temperature of 150° C. at 4-mm Hg absolute pressure to give 173 g of BHMO, representing a 97% yield.

An acetyl nitrate solution was prepared by adding, with stirring, 167 ml of 90-percent nitric acid to 600 ml of acetic anhydride at 20° C. This solution was then cooled to 5° C. and added slowly with vigorous stirring to a solution of 167 g of BHMO in 1400 ml of methylene chloride. The temperature was maintained at −10° C. during the addition and for a further 15 to 30 minutes thereafter. The reaction was quenched by pouring over 900 g of sodium bicarbonate followed by the addition of water and very rapid stirring. When the pH of subsequent bicarbonate-water washings remained at 7 to 8, the organic layer was washed with distilled water and dried over magnesium sulfate. The solid product isolated after removal of the solvent was recrystallized in carbon tetrachloride. The final yield was 215 g or a 73 percent yield at polymerizable purity. Elemental analysis confirmed that the product was BNMO.

Obviously, many modifications and variations of the present invention are possible in light of the above teachings. It is therefore to be understood that within the scope of the appended claims, the invention may be practiced otherwise than as specifically described.

We claim:

1. A method of synthesizing a nitrato alkyl oxetane comprising:

nitrating a hydroxy alkyl oxetane of the general formula

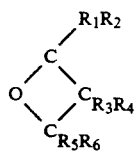

wherein at least one of $R_1-R_2$ is $-(CH_2)_n-CHOH-A$, wherein n is one or greater and A is selected from the group comprising H and alkyl groups and the remainder of $R_1-R_6$ are selected from the group comprising H and alkyl, under non-acidic anhydrous conditions with an anhydrous nitrate ester of a carboxylic acid of the general formula R—COOH wherein R is an alkyl or aryl moiety.

2. A method as described in claim 1 wherein A is H.

3. A method as described in claim 2 wherein n is between one and three.

4. A method as described in claim 3 wherein the hydroxy alkyl oxetane is 3,3-bis(hydroxymethyl)oxetane.

5. A method as described in claim 3 wherein the hydroxy alkyl oxetane is 3-hydroxymethyl-3-methyloxetane.

6. A method as described in claim 1 wherein said carboxylic acid is acetic acid.

7. A method as described in claim 1 wherein said nitration is carried out at a temperature of below about 10° C.

8. A method as described in claim 7 wherein said nitration is carried out at a temperature of between about 10° and −20° C.

9. A method as described in claim 8 wherein said nitration is carried out at a temperature of about 0° C.

10. A method as described in claim 1 wherein said nitration is carried out in a non-reactive, non-hygroscopic organic solvent.

11. A method as described in claim 9 wherein the solvent is chloroform or methylene chloride.

12. A method as described in claim 1 wherein the anhydrous nitrate ester is formed by reacting a nitrate-containing compound with an anhydride of the carboxylic acid.

13. A method as described in claim 12 wherein the nitrate-containing compound is between about 90% and 100% nitric acid.

14. A method as described in claim 13 wherein the nitrate-containing compound is about 90% nitric acid.

* * * * *